United States Patent [19]

Yates et al.

[11] Patent Number: 5,188,111

[45] Date of Patent: Feb. 23, 1993

[54] DEVICE FOR SEEKING AN AREA OF INTEREST WITHIN A BODY

[75] Inventors: David C. Yates, Indianapolis; William C. McCoy, Zionsville, both of Ind.

[73] Assignee: Catheter Research, Inc., Indianapolis, Ind.

[21] Appl. No.: 642,882

[22] Filed: Jan. 18, 1991

[51] Int. Cl.$^5$ ............................................. A61M 25/00
[52] U.S. Cl. ..................... 128/657; 604/281;
604/95; 128/662.26; 128/DIG. 7; 606/78
[58] Field of Search .............. 128/4, 6, 656, 657,
128/772; 604/264, 280, 281, 95; 606/78

[56] References Cited

U.S. PATENT DOCUMENTS

| | | |
|---|---|---|
| 4,589,404 | 5/1986 | Barath et al. |
| 4,641,650 | 2/1987 | Mok |
| 4,682,594 | 7/1987 | Mok |
| 4,754,328 | 6/1988 | Barath et al. |
| 5,090,956 | 2/1992 | McCoy ........................ 604/95 |

OTHER PUBLICATIONS

1990 Confidential Memorandum: p. 27 (redacted).

*Primary Examiner*—Kyle L. Howell
*Attorney, Agent, or Firm*—Barnes & Thornburg

[57] ABSTRACT

An assembly is provided for seeking an area of interest within a body. The assembly includes an elongated directable member having a distal end for insertion into the body. The distal end includes a tip portion. The assembly also includes a deflector coupled to the directable member for deflecting the distal end of the directable member to direct the directable member within the body. The assembly further includes a sensor located in close proximity to the top portion of the directable member for sensing an area of interest within the body. The sensor generates an indicator signal upon detection of the area of interest. The assembly still further includes a control unit coupled to the deflector for controlling deflection of the distal end of the directable member by the deflector. The control unit generates a control signal to drive the deflector. The control unit stops deflection of the distal end of the directable member in response to the indicator signal generated by the sensor upon detection of the area of interest. The control unit holds the tip portion of the directable member in a stationary position directed toward the area of interest.

20 Claims, 4 Drawing Sheets

DEVICE FOR SEEKING AN AREA OF INTEREST WITHIN A BODY

BACKGROUND AND SUMMARY OF THE INVENTION

The present invention relates to a device for seeking an area of interest within a body. More particularly, the present invention relates to a control system for guiding a sensing device through cavities in a body to automatically seek out and locate an area of interest within the body.

Detection, diagnosis, and treatment of damaged or diseased tissues within a human body is often difficult. In addition, inspection of industrial or mechanical devices to look for defects or damage can also be difficult, especially if the device is located in a harsh environment or in a place having restricted or limited access. It is therefore desirable to produce a device which automatically locates an area of interest within a body and alerts an operator that the area of interest has been detected so that an analysis, diagnosis, treatment, or repair decision can be made by the operator or by a diagnostic or therapeutic mechanism.

It is known to provide temperature-activated memory elements coupled to a distal end of a catheter to steer the catheter through cavities in a body. By selectively controlling the heating of the memory elements, an operator can deflect the distal end of the catheter to steer the catheter through cavities in the body. A controller for controlling electrical current to the memory elements is typically used to control the temperature of selected memory elements from a remote position outside the body to deflect the distal end of the catheter in a plurality of different directions corresponding to the preset shapes of the memory elements. This permits an operator to steer the catheter through body cavities. See, for example, U.S. Pat. Nos. 4,543,090; 4,601,705; 4,758,222; and 4,944,727.

In addition, various types of sensing devices and treating devices are known which can be positioned inside a catheter. These sensors can be used to detect arterial plaque, atherosclerotic, tumorous, or otherwise diseased or damaged tissues within a body. Various types of treatment devices can also be connected to a catheter to treat damaged or diseased tissue. See, for example, U.S. Pat. Nos. 4,641,650; 4,682,594; and 4,785,806.

One object of the present invention is to provide a device that will automatically seek out an area of interest within the body and provide an indication of the specific location of the area of interest inside the body.

Advantageously, the present invention provides a device capable of locating an area of interest within a harsh environment to minimize exposure of an operator to the harsh environment or within an area having limited access to permit analysis.

According to the present invention, an assembly for seeking an area of interest within a body includes an elongated directable member including a distal end for insertion into the body. The distal end includes a tip portion. The assembly also includes deflecting means coupled to the directable member for deflecting the distal end of the directable member to direct the directable member within the body. The assembly further includes sensing means located in close proximity to the tip portion of the directable member for sensing an area of interest within the body. The sensing means generates an indicator signal upon detection of the area of interest. The assembly still further includes controlling means coupled to the deflecting means for controlling deflection of the distal end of the directable member by the deflecting means. The controlling means generates a control signal to drive the deflecting means. The controlling means stops deflection of the distal end of the directable member by the deflecting means in response to the indicator signal generated by the sensing means upon detection of the area of interest. The controlling means holds the tip portion of the directable member in a stationary position directed toward the area of interest. Means for coupling the sensing means to the controlling means is also provided.

In an illustrated embodiment of the present invention, the deflecting means includes at least one temperature activated memory element coupled to the distal end of the directable member and means coupled to the at least one memory element for selectively heating the at least one memory element to deflect the distal end of the directable member. The heating means is coupled to the controlling means.

The deflecting means generates a control signal for deflecting the distal end of the directable member. The assembly further includes means for mapping the location of the area of interest inside the body. The deflecting means is coupled to the mapping means. The mapping means includes means for storing the output of the sensor and the control signal output of the deflecting means.

In another illustrated embodiment of the present invention, the assembly includes treating means located near the tip portion of the directable member for treating the area of interest. A treatment source is coupled to the treating means for delivering a treatment to the area of interest through the treating means after the tip portion of the directable member is directed toward the area of interest and held in position by the controlling means.

In yet another illustrated embodiment, the assembly includes imaging means located near the tip portion of the directable member for providing an image signal representing the area of interest. The assembly still further includes means for storing the image signal provided by the imaging means upon detection of the area of interest by the sensing means.

In a further illustrated embodiment of the present invention, the assembly includes calculating means coupled to the sensor for calculating the dimensions of the area of interest detected by the sensor. The calculating means includes means for measuring the deflection angle of the distal end relative to the elongated directable member and means for determining the distance between the area of interest and the distal end of the directable member. The calculating means calculates the change in the deflection angle of the distal end of the directable member to measure the dimensions of the area of interest only during the generation of the indicator signal by the sensor.

In a still further illustrated embodiment of the present invention, the assembly includes means for scanning the area of interest upon detection of the area interest by the sensor. The scanning means directs the distal end of the directable member at a portion of the area of interest which has the desired magnitude of a predetermined characteristic detected by the sensor. The scanning means includes means for sampling the magnitude of the predetermined characteristic at selected intervals along the area of interest as the distal end of the directable member scans the area of interest. The sampled magnitudes are stored in a memory of the scanning means. The scanning means also includes means for comparing the magnitudes of the stored samples to determine which sample or group of samples has the desired magnitude. The scanning means returns the distal end of the directable member to the portion of the area of interest having the desired magnitude of the predetermined characteristic after the entire area of interest has been scanned.

In this specification and in the claims, the word "body" is intended to refer to various types of bodies in which the device of the present invention can be used including a human body, mechanical devices, machines, or other environments in which the present invention would be beneficial.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
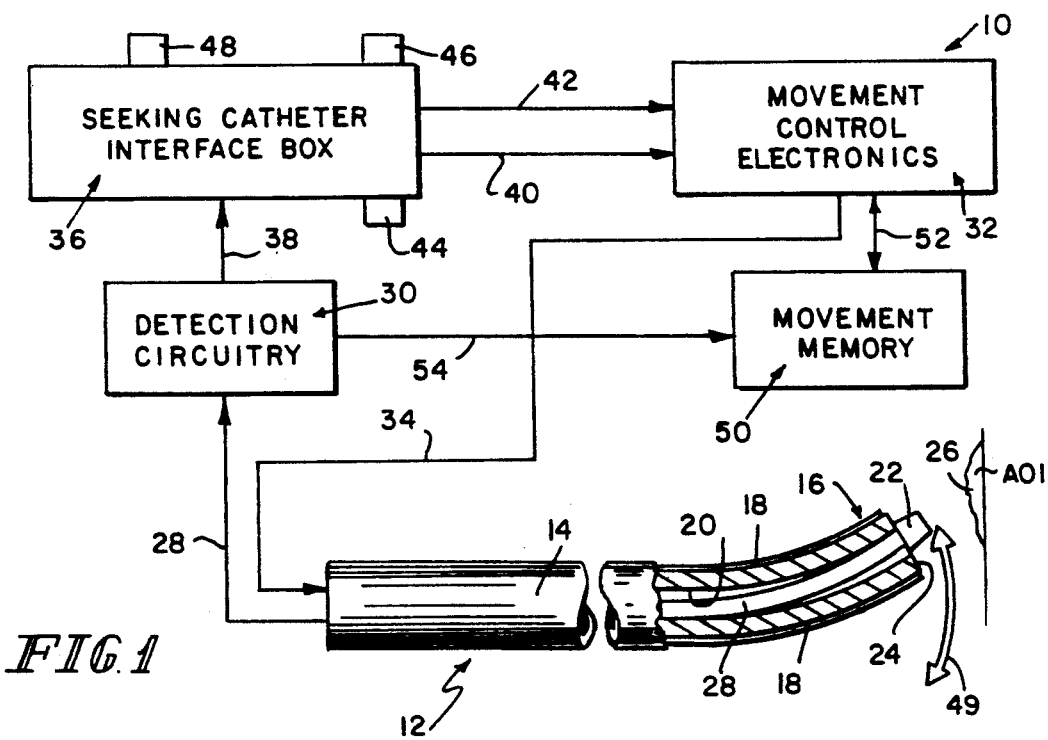
FIG. 1 is a diagrammatical illustration of a control system according to the present invention for directing the directable member or catheter through a body to seek out and locate an area of interest.

A control system 10 embodying the present invention is shown generally in FIG. 1. A directable member or catheter 12 includes an elongated tubular member 14 having a directable distal end 16 designed to be inserted into a body. Temperature-activated memory elements 18 are incorporated into or coupled to the distal end 16 of tubular member 14. The memory elements 18 may be wires or flat strips formed from a mechanical shape memory metal such as nickel titanium alloy or other type of material having shape memory characteristics. Typically, memory elements 18 are pliable until they are heated above a predetermined transitional temperature at which time they begin to assume a predetermined shape thereby exerting a predetermined force to move the tip of the catheter. Illustratively, catheter 12 is a catheter Model 8080 available from Catheter Research, Inc. of Indianapolis, Ind., which is more particularly described in U.S. Pat. Nos. 4,543,090; 4,601,705; and 4,758,222. As disclosed in one or more of these patents, a plurality of memory elements 18 could be used to move the distal end 16 in a plurality of different directions or a single memory element 18 combined with a spring (not shown) could also be used.

Tubular member 14 of catheter 12 is formed to include a lumen 20 extending the entire length of catheter 12. A detection element or sensor 22 is located at the distal end 16 of catheter 12 near tip portion 24 of catheter 12. Sensor 22 senses or detects an area of interest (AOI) 26 located within the body. A suitable connector 28 connects sensor 22 to detection circuitry 30. The signal is then transmitted through connector 28 which may include an electrical or mechanical connector, fiber optic bundle, or other type of suitable signal transmission means. Sensor 22 generates a control signal which passes through connector 28 to detection circuitry 30 upon detection of an area of interest 26 within the body. The sensor 22 can be chosen to detect any type of area of interest 26 depending on the particular application in which the system 10 is being used.

Catheter 12 which includes sensor 22 can be used inside a human body, as an inspection device in industrial or commercial devices or in other types of diagnostic devices. As discussed above, various types of sensors 22 can be used with the present invention. Types of sensors 22 that may be used include, for example, electrical potential, luminescence, fluorescence, optical, chemical, radiation, composition, concentration, pH, or gas sensors such as ChemFET sensors. Sensors 22 can be used for ultrasonic imaging profiles or densities; x-ray imaging profiles or densities including CAT scans; nuclear medicine imaging profiles, densities, or concentrations; and magnetic resonance imaging profiles, densities, chemical compositions, or concentrations. In addition, temperature sensors, tactile sensors, pressure sensors, flow sensors, vibration or other acoustical data sensors can be used. This list of sensors 22 which can be used with the present invention is intended to be illustrative and is not to be considered an exhaustive list.

In operation, the distal end 16 of tubular member 14 is inserted into a body cavity (not shown) while memory elements 18 are relaxed or pliable and at a temperature below the transitional temperature of the memory elements. This facilitates insertion of distal end 16 into the body cavity. Movement control electronics 32 are connected to the catheter 12 by a suitable connector 34. The movement control electronics 32 supply a controlled power source to the memory elements 18 to heat the memory elements 18 above the transitional temperature to deflect or move the distal end 16 of tubular member 14 in a predetermined direction. When the memory elements 18 are heated above their transitional temperature, they remain relatively stiff and are situated in a preset shape. When the memory elements 18 cool to a temperature below the predetermined transitional temperature, they become soft and pliable. Movement control electronics 32 and memory elements 18 provide the deflecting means of the present invention. Movement control electronics 32 also controls the rate of deflection of distal end 16. Illustratively, movement control electronics 32 is a CRI Model CS106 control electronics package available from Catheter Research, Inc. It is understood that other methods may be used to control movement of catheter 12 inside the body.

The control system 10 of the present invention also includes a seeking catheter interface box 36 connected between detection circuitry 30 and movement control electronics 32. The circuitry inside the seeking catheter interface box 36 provides the controlling means of the present invention. The output 38 of detection circuitry 30 is coupled to an input of the interface box 36. Two outputs 40 and 42 interconnect the interface box 36 with the movement control electronics 32. As discussed below, user enable switch 48 must be closed before movement of the catheter 12 begins. A first sweep command switch 44 on interface box 36 is closed to connect the output signal from interface box 36 to the movement control electronics 32 by connector 40. A second sweep command switch 46 located on interface box 36 is closed to connect the output signal from interface box 36 to movement control electronics 32 by connector 42. First switch 44 causes the interface box 36 to generate a control signal to drive movement control electronics 32 through connector 40 to deflect the distal end 16 of catheter 12 in a first direction. Second switch 46 connects the control signal from interface box 36 to drive control electronics 32 by connector 42 to deflect the distal end 16 of catheter 12 in a second predetermined direction different than the first direction. As discussed below, the output of sensor 22 can be used to control movement of the distal end 16 without the use of switches 44 and 46.

After the catheter 12 is inserted into the body, the sweep direction is selected by an operator by closing either switch 44 or switch 46. A user enable switch 48 is closed to begin deflection of the distal end 16 of catheter 12. As the catheter 12 is fed through the body by an operator or by an automatic feeding mechanism, the distal end 16 sweeps to different deflection angles as indicated by double headed arrow 49. For example, the deflection angles could be any angle in a range of 0°–90°. The operator or automatic feeding mechanism can control the direction that the distal end 16 points by twisting or rotating the catheter 12 about its longitudinal axis.

When sensor 22 detects an area of interest 26 inside the body, an indicator signal is generated which passes through connector 28 to detection circuitry 30. Detection circuitry 30 generates a signal indicative of the detection of the area of interest 26 by sensor 22. Detection circuitry 30 is connected to interface box 36 by connector wire 38. When detection circuitry 30 generates a control signal indicative of the detection of area interest 26 by sensor 22, interface box 36 generates a control signal to "freeze" or hold the distal end 16 of catheter 12 in a stationary position directed toward the area of interest 26. After the tip portion 24 of catheter 12 is directed at the area of interest 26, an operator or a diagnostic or therapeutic mechanism can make a diagnosis or treatment decision for the particular area of interest 26. The FIG. 1 embodiment can include a treatment device (not shown) such as the treatment device 70 illustrated in FIG. 4 discussed below to treat the area of interest 26 after it is located.

A data storage or memory device 50 illustrated in FIG. 1 is used to record the control signal generated by movement control electronics 32 which controls deflection of distal end 16 of catheter 12. An output from movement control electronics 32 is coupled to movement memory device 50 by connector 52. By recording the control signal, it is possible for another subsequently inserted catheter to follow the same path through the body as the catheter 12 to reach the detected area of interest 26 within a body at a later time. This may be particularly advantageous when a separate treatment catheter (not shown) is used to treat an area of interest 26. After catheter 12 detects an area of interest 26 and the control signal from movement control electronics 32 is stored in the memory device 50, the catheter 12 is removed from the body. A treating catheter (not shown) can then be inserted into the body, and the stored control signal can be retrieved from memory 50 and used to guide the treatment catheter to the precise location of the area of interest 26 within the body so that the area of interest 26 can be treated.

An output from detection circuitry 30 is also coupled to movement memory 50 by connector 54. Movement memory 50 records the output from sensor 22 at a particular location to map the location of an area of interest 26 or multiple areas of interest 26 within the body. By storing information about the position of the catheter 12 within the body and information from the sensor 22, movement memory 50 can be used to generate a graph or a map of the locations of one or more areas of interest 26 within the body.

Figure 2:
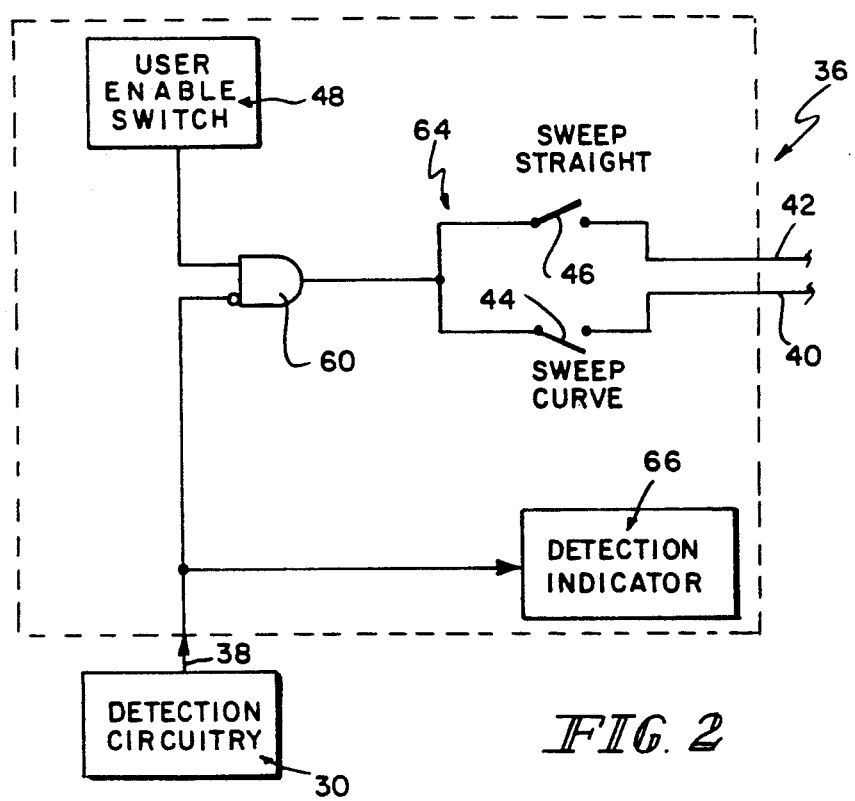
FIG. 2 is a block diagram of the control circuitry of the present invention for controlling movement of the directable member through the body.

A block diagram of the control circuitry in the seeking catheter interface box 36 is illustrated in FIG. 2. Detection circuitry 30 generates a logical one output signal when sensor 22 detects an area of interest 26 within the body. The output of the detection circuitry 30 is inverted and connected to one input of AND gate 60. A second input of AND gate 60 is connected to user enable switch 48. When closed, user enable switch 48 generates a logical one signal.

The output of AND gate 60 is connected to switch means 64 for controlling the direction of deflection of distal end 16 of catheter 12. First sweep command switch 44 and second sweep command switch 46 are alternately opened and closed to move the distal end 16 of catheter 12 within the body so that the sensor 22 scans the area around the tip portion 24 to detect an area of interest 26. When an area of interest 26 is detected, detection circuitry 30 generates a logical one signal which activates detection indicator 66. Detection indicator 66 provides an audible and/or visual indication that the area of interest 26 has been detected.

Figure 3:
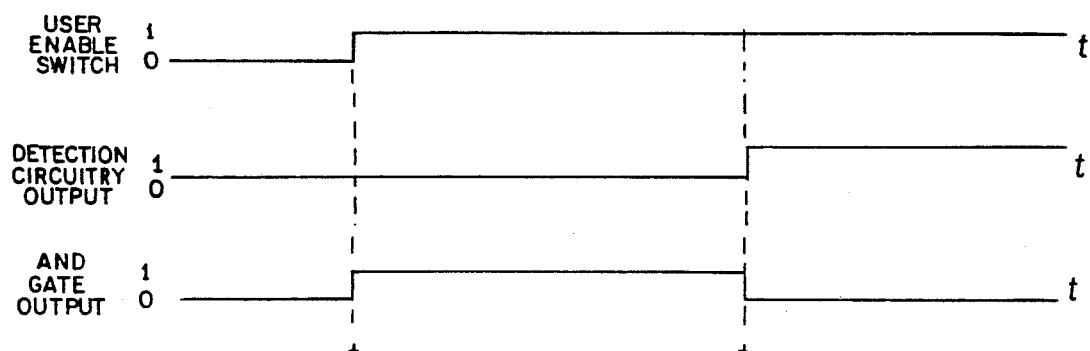
FIG. 3 is a timing diagram illustrating the outputs of various control signals of the control system of the present invention.

FIG. 3 illustrates the timing diagram of various control signals of the control system 10. The control circuitry in interface box 36 generates a logical one control signal to deflect distal end 16 of catheter 12 only when a logical one output is generated by AND gate 60. When the output of AND gate 60 is logical zero, interface box 36 generates a logical zero control signal to hold the distal end 16 of catheter 12 in a stationary position.

The outputs of user enable switch 48, detection circuitry 30, and AND gate 60 are all illustrated in FIG. 3. Before time $t_1$, the user enable switch 48 is open so that a logical zero output is produced. The detection circuitry 30 output is also logical zero indicating that an area of interest 26 has not yet been detected by sensor 22. The inverse of the detection circuitry 30 output is coupled to AND gate 60. Therefore, the output of AND gate 60 is a logical zero output prior to time $t_1$.

At time $t_1$, user enable switch 48 is closed to generate a logical one control signal. After time $t_1$, and while output of detection circuitry 30 remains a logical zero, the AND gate 60 output is a logical one. This is because the output of detection circuitry 30 is inverted before being connected to AND gate 60. From time $t_1$ to time $t_2$, AND gate 60 generates a control signal to move the distal end 16 of catheter 12 in a predetermined direction controlled by switches 44 and 46. The movement control electronics 32, when provided with the control signal from AND gate 60, will produce a controlled power output to deflect the distal end 16 of catheter 12. The rate of deflection is also controlled by the movement control electronics 32.

At time $t_2$, the sensor 22 detects an area of interest 26 within the body and detection circuitry 30 generates a logical one control signal. This signal is inverted and input into AND gate 60. Therefore, after the area of interest 26 is detected at $t_2$, the output of AND gate 60 becomes a logical zero to hold the distal end 16 of catheter 12 in a stationary position with tip portion 24 directed at the area of interest 26.

The seeking devices of the present invention can be designed to seek out an area of interest in a harsh environment which is potentially harmful to humans. This area of interest may include a radioactive area or other dangerous condition in which it is desirable to minimize contact of the environment with an operator. The transitional temperature of the memory elements can be set at various temperatures using different processing and annealing techniques. Therefore, the system of the present invention is capable of being used to detect leaks of radiation, chemicals, electrical fields, or other such problems in a harsh environment while minimizing the possibility of exposure of an operator to the harsh environment.

Figure 4:
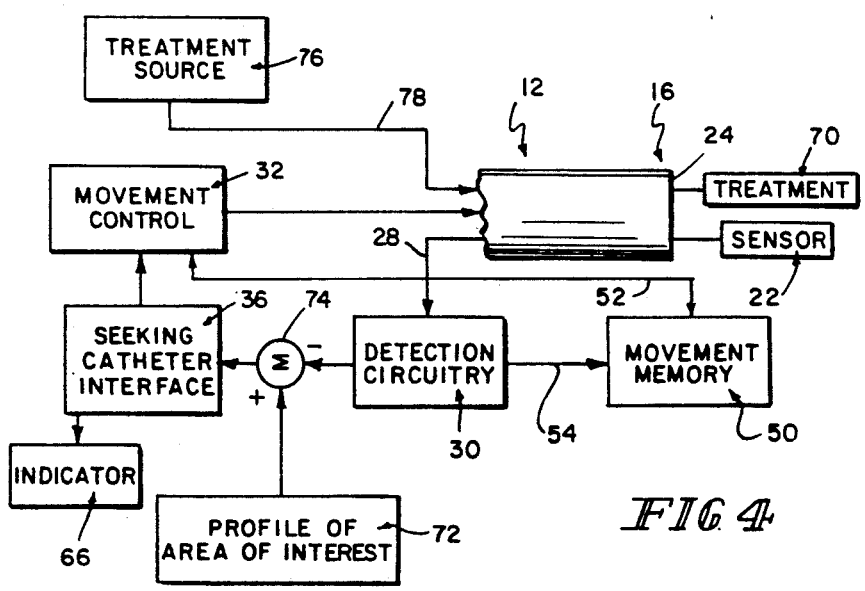
FIG. 4 is a diagrammatical illustration of another embodiment of the present invention which includes a treatment device and a sensor device located near the tip portion of the directable member.

Another embodiment to the present invention is illustrated in FIG. 4. Those elements referenced by numbers identical to those used in FIGS. 1-5 perform the same or similar function. In FIG. 4, the catheter 12 includes a sensor 22 and a treatment device 70 located near tip portion 24 at distal end 16 of deflectable member or catheter 12. In addition to the sensors discussed above, sensor 22 may be a chemical sensor, a spectroscopy sensor, or an encapsulated coil such as a magnetic resonance imaging coil which provides an image signal of the profile of areas within the body. These sensors 22 can be used to provide a visual, chemical, or electrical analysis of the area within the body without the need for a tissue biopsy.

The output of detection circuitry 30 is compared to a reference signal indicative of a profile of a particular area of interest that the operator is trying to detect. The reference signal is generated by signal generator 72. Comparison between detection circuity 30 and the reference signal 72 is made by comparator 74. The output of comparator 74 is used to drive seeking catheter interface box 36 in a manner similar to that described above with regard to FIGS. 1-5. When the output of detection circuitry 30 substantially matches the profile of the area of interest from generator 72, the seeking catheter interface 36 stops movement of the distal end 16 of catheter 12 by a movement control electronics 32 to hold the tip portion 24 of catheter 12 in a stationary position directed at the area of interest. Indicator 66 provides an audible and/or visual indication that the area of interest has been detected by sensor 22.

The system of FIG. 4 of the present invention maintains the tip portion 24 of catheter 12 directed at the area of interest 26 even upon movement of the catheter 12 or the body after detection of the area of interest 26. If the tip portion 24 moves away from the area of interest 26 because of movement of the body or catheter 12, the sensor 22 will no longer generate the indicator signal to hold the tip of the catheter in place. Therefore, the tip portion 24 of catheter 12 begins to move until the tip portion 24 is again directed at the area of interest 26 and the sensor 22 generates the indicator signal to stop the deflection of the tip portion 24. If the output from comparator 74 is a positive valve, the distal end 16 is deflected in a first direction. If the output of comparator 74 is negative, the distal end is deflected in a second direction different from the first direction. An output of substantially zero from comparator 74 stops deflection of distal end 16.

Tip portion 24 of catheter 12 is held in a position directed at the area of interest so that an operator or a mechanism can make a diagnosis and a treatment decision on the area of interest 32. While tip portion 24 is directed at the area of interest 26, an operator or mechanism can treat the area of interest 26 with treatment device 70. Treatment device 70 is connected to a treatment source 76 located outside the body by a suitable connector 78. Illustratively, treatment device 70 can be in the form of ablation, abrasion, chemical, medicinal, electrical, electrocautery, bovie knife, radio frequency, microwaves, or other types of therapy.

Other examples of possible treatments to be applied once an area of interest is detected include laser treatment, hot tips for thermal treatment, stents, occlusion coils, balloons, plugs, glue, silicone, patching, baskets for collecting stones, chemotherapy, or radiation treatment. Other possible treatments which can be delivered using the system of present invention include contrast media for x-ray, CT, magnetic resonance, etc.; isotopes for nuclear medicine or imaging, fiber optics for observation, analysis, or treatment; devices to obtain biopsy samples; or markers or dyes for medical imaging. In addition, devices to apply pressure in the form of a push, devices to sever or cut lesions from the body, and ultrasonic probes, can also be used. This list is illustrative only and is not meant to be exhaustive.

A data storage or memory device 50 illustrated in FIG. 4 is used to record the control signal generated by movement control electronics 32 which controls deflection of distal end 16 of catheter 12. An output from movement control electronics 32 is coupled to movement memory device 50 by connector 52. By recording the control signal, it is possible for another subsequently inserted catheter to follow the same path through the body as the catheter 12 to reach the detected area of interest 26 within a body at a later time.

An output from detection circuitry 30 is also coupled to movement memory 50 by connector 54. Movement memory 50 records the output from sensor 22 at a particular location to map the location of an area of interest 26 or multiple areas of interest 26 within the body. By storing information about the position of the catheter 12 within the body and information from the sensor 22, movement memory 50 can be used to generate a graph or a map of the locations of one or more areas of interest 26 within the body.

Figure 5:
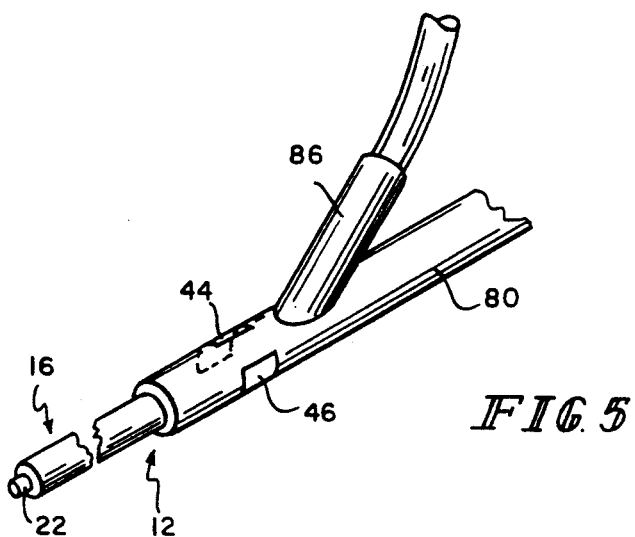
FIG. 5 is a perspective view illustrating control switches located on a hub of a catheter to facilitate operation of the device.

Another embodiment of the present invention is illustrated in FIG. 5. In this embodiment, the first sweep command switch 44 and second sweep command switch 46 are located on the hub 80. All the control electronics are located in module 86. This embodiment would permit an operator to insert the catheter 12 into the body and control deflection of the distal end 16 of catheter 12 using only one hand. Therefore, the operator's other hand could be used for other activities.

Figure 6:
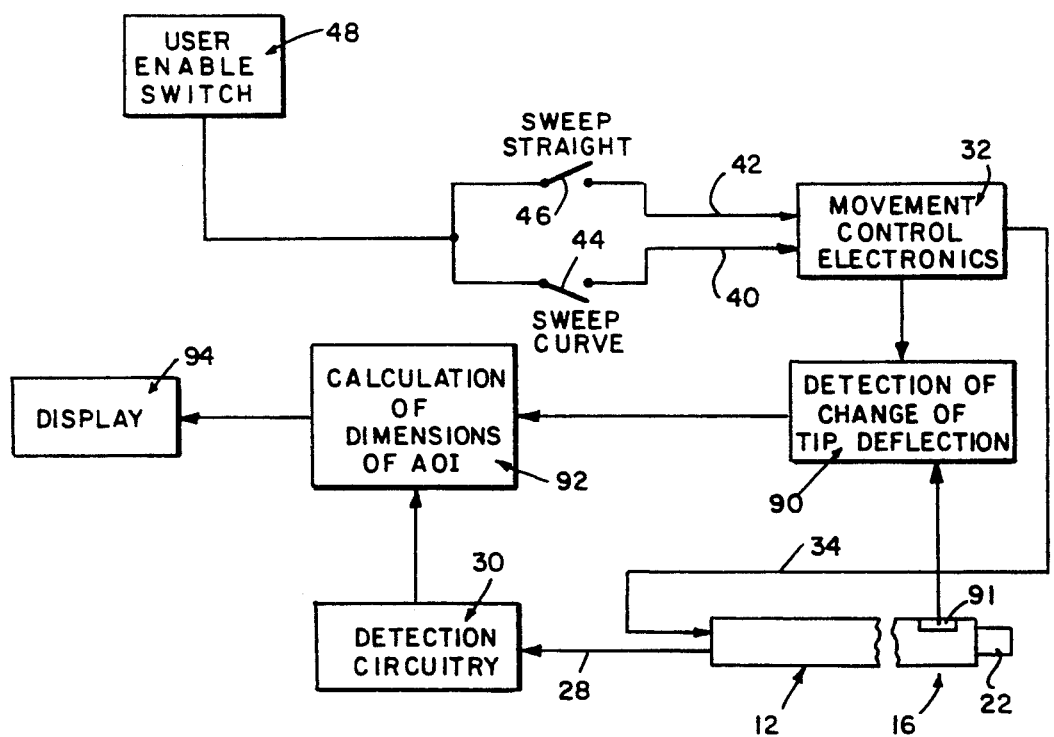
FIG. 6 is a diagrammatical illustration of yet another embodiment of the present invention including electronics for calculating the dimensions of an area of interest inside the body.

Another embodiment of the present invention is illustrated in FIG. 6. Those elements referenced by numbers identical to those used in FIGS. 1-5 perform the same or similar function. The movement control electronics 32 operate to deflect the distal end 16 of catheter 12 inside the body. User enable switch 48 is coupled to movement control electronics 32 by first sweep command switch 44 and second sweep command switch 46 through connectors 40 and 42, respectively. The embodiment illustrated in FIG. 6 includes a detection circuit 90 for detecting the change in the deflection angle of the distal end 16 of catheter 12. Circuit 90 is illustratively an A/D convertor, a D/A convertor, or an operational amplifier. The change in the deflection angle of the distal end 16 of catheter 12 can also be detected by a Hall Effect sensor, a strain garage, or a piezo-electric switch located near the distal end 16 of catheter 12 as indicated at location 91. An input of detection circuitry 90 is coupled to movement control electronics 32. An output of detection circuitry 90 is coupled to a circuit 92 for calculating the dimensions of the area of interest within the body. When an area of interest is detected by sensor 22, detection circuitry 30 generates a logical one indicator signal. Detection circuity 30 is coupled to second input of circuit 92. Circuit 92 calculates the dimensions of deflection of the distal end 16 of catheter 12 during the time that the logical one indicator signal is received from detection circuitry 30 indicating that an area of interest has been detected. This embodiment does not stop deflection of the distal end 16 of catheter 12 after detection of the area of interest. Calculation of the dimensions occurs only during detection of the area of interest by sensor 22. Circuit 92 calculates the total change in the deflection angle of the tip portion 24 of catheter 12 in order to calculate the dimensions of the area of interest. Illustratively, circuit 92 is a conventional microcontroller or a conventional microprocessor such as, for example, an 80C51 microprocessor available from Intel Corporation using software to calculate the dimensions. Therefore, circuit 92 calculates the arc length of the area of interest 26. By determining the distance from the tip portion 24 of catheter 12 and the area of interest 26, the dimensions of the area of interest can be calculated once the arc length of the area of interest 26 is known. A display 94 can be used to provide a visual indication of the dimensions of the area of interest 26 detected within the body.

Figure 7:
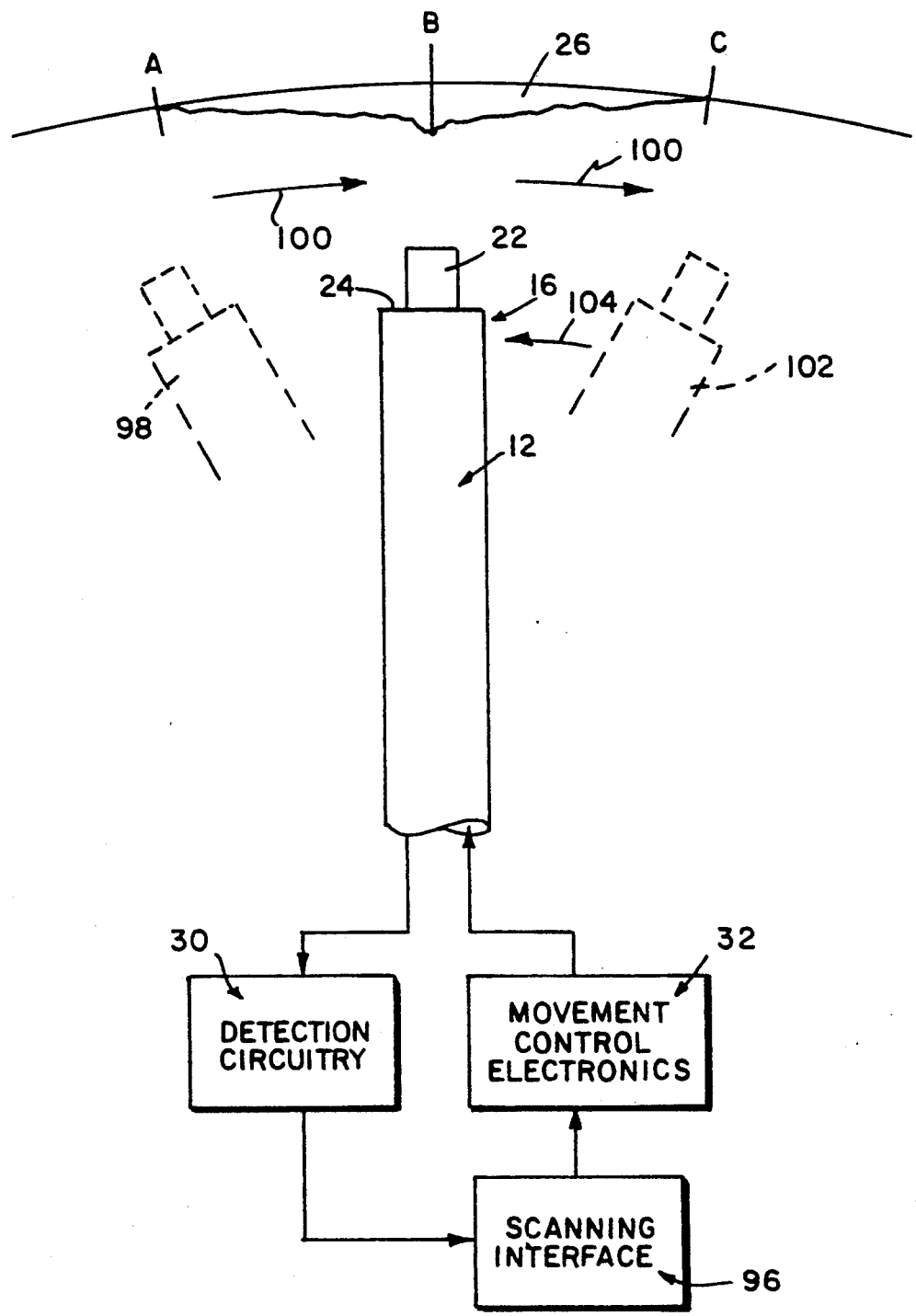
FIG. 7 is a diagrammatical illustration of a further embodiment of the present invention including means for scanning the area of interest to direct the distal end of the directable member at a selected portion of the area of interest

Yet another embodiment of the present invention is illustrated in FIG. 7. In this embodiment, the sensor 22 coupled to catheter 12 scans the entire area of interest 26 and aligns the tip portion 24 of the catheter at the portion of the area of interest which has the highest magnitude of a desired characteristic. A scanning interface 96 is coupled between the output of detection circuitry 30 and the input of movement control electronics 32. In FIG. 7 the area of interest 26 begins at location A and has its highest magnitude of the predetermined characteristic at location B. The area of interest 26 ends at location C. In operation, sensor 22 detects the area of interest 26 beginning at location A when the catheter 12 is oriented in the position indicated by broken lines 98. The distal end 16 of catheter 12 is deflected by movement control electronics 32 in the direction of arrows 100 so that sensor 22 scans the entire area of interest 26. When catheter 12 is in the orientation illustrated by broken lines 102, the sensor 22 has scanned the entire area of interest 26. As the distal end 16 scans the area of interest 26, scanning interface 96 samples the magnitude of the predetermined characteristic of the area of interest 26 either continuously or at predetermined intervals. The values of these samples are stored so that the magnitude of the area of interest 26 at any given location is known. After the entire area of interest 26 has been scanned, scanning interface 96 controls the movement control electronics 32 to deflect the distal end 16 of catheter 12 in the direction of arrow 104 to return the sensor 22 and tip portion 24 to a position directed toward the portion B of area of interest 26 which has the desired magnitude of the predetermined characteristic. The FIG. 7 embodiment can include a treatment device (not shown) such as treatment device 70 illustrated in FIG. 4. This permits a treatment source to be directed toward the portion of the area of interest 26 which has the desired magnitude so that treatment can be most effective. Illustratively, sensor 22 can detect the portion of the area of interest 26 which has the highest concentration. A luminescence or flourluminescence sensor can be used to detect the portion of the area of interest 26 which provides the most luminescence. Various other desired characteristics can be determined and located. The sensor can also be aligned so that it is directed toward the area with the highest temperature, the lowest temperature, the highest or lowest density. Additionally, a value within a specific range can be located.

In the embodiment of the invention shown in FIG. 7, the output of sensor 22 controls the deflection of the distal end 16 of catheter 12. The direction of deflection is therefore not controlled by switches. The output of sensor 22 can be used to control the direction of deflection of the distal end 16 of catheter 12.

Although the invention has been described in detail with reference to certain preferred embodiments, variations and modifications exist within the scope and spirit of the invention as described in and defined in the following claims.

What is claimed is:

1. An assembly for seeking an area of interest within a body, the assembly comprising
   an elongated directable member having a distal end for insertion into the body, the distal end including a tip portion,
   deflecting means coupled to the directable member for deflecting the distal end of the directable member to direct the directable member within the body,
   sensing means located in close proximity to the tip portion of the directable member for sensing an area of interest within the body, and generating an indicator signal upon detection of the area of interest, and
   controlling means coupled to the deflecting means for controlling deflection of the distal end of the directable member by the deflecting means and generating a control signal to drive the deflecting means, the controlling means including means for stopping deflection of the distal end of the directable member by the deflecting means in response to the indicator signal generated by the sensing means upon detection of the area of interest.

2. The assembly of claim 1, wherein the controlling means holds the tip portion of the directable member in a stationary position directed toward the area of interest during detection of the area of interest by the sensing means.

3. The assembly of claim 1, wherein the deflecting means includes at least one temperature activated memory element coupled to the distal end of the directable member and means coupled to the at least one memory element for selectively heating the at least one memory element to deflect the distal end of the directable member, the heating means being coupled to the controlling means.

4. The assembly of claim 3, wherein the assembly includes two memory elements coupled to the distal end of the directable member and the controlling means includes first switch means for coupling the controlling means to the deflecting means to cause the deflecting means to deflect the distal end of the directable member in a first direction, and the controlling means also includes second switch means for coupling the controlling means to the deflecting means to cause the deflecting means to deflect the distal end of the directable member in a second direction different than plurality of memory element the first direction.

5. The assembly of claim 3, wherein the assembly includes a plurality of memory elements coupled to the distal end of the directable member for deflecting the distal end of the directable member in a plurality of different directions.

6. The assembly of claim 1, wherein the controlling means generates a control signal for deflecting the distal end of the directable member, the assembly further comprising means for mapping the location of the area of interest inside the body, and means for coupling the controlling means to the mapping means.

7. The assembly of claim 6, wherein the mapping means includes means for storing the output of the sensor and the control signal output of the controlling means.

8. The assembly of claim 1, further comprising treating means located near the tip portion of the directable member for treating the area of interest.

9. The assembly of claim 8, further comprising a treatment source coupled to the treating means for delivering a treatment to the area of interest through the treating means when the tip portion of the directable member is directed toward the area of interest.

10. The assembly of claim 1, further comprising an indicator for providing an indication that the area of interest has been detected by the sensing means, and means for coupling the indicator to the sensing means.

11. The assembly of claim 1, further comprising imaging means located near the tip portion of the directable member for providing an image signal representing the area of interest.

12. The assembly of claim 11, further comprising means for storing the image signal provided by the imaging means upon detection of the area of interest by the sensing means, and means for coupling the imaging means to the means for storing the image signal.

13. An assembly for seeking an area of interest within a body, the assembly comprising
an elongated directable member including a distal end for insertion into the body and at least one temperature activated memory element coupled to the distal end, the memory element moving to assume a predetermined shape when heated to a predetermined temperature,
heating means for heating the at least one memory element to deflect the distal end of the directable member to direct the directable member within the body,
means for coupling the heating means to the at least one temperature activated memory element,
a sensor located in close proximity to the distal end of the directable member for detecting an area of interest within the body,
controlling means coupled to the heating means for controlling deflection of the distal end of the directable member by the heating means and generating a first control signal to cause the heating means to deflect the distal end of the directable member, and the controlling means including means for generating a second control signal to cause the heating means to hold the distal end of the directable member in a stationary position directed toward the area of interest upon detection of the area of interest by the sensor, and
means for coupling the sensor to the controlling means.

14. The assembly of claim 13, wherein the assembly includes two memory elements coupled to the distal end of the directable member, the controlling means includes first switch means for coupling the controlling means to the heating means to cause the heating means to deflect the distal end of the directable member in a first direction, and the controlling means includes second switch means for coupling the controlling means to the heating means to cause the heating means to deflect the distal end of the directable member in a second direction different than the first direction.

15. The assembly of claim 13, further comprising means for mapping the location of the area of interest inside the body.

16. The assembly of claim 15, wherein the mapping means includes means for storing the output of the sensor and the output of the controlling means.

17. The assembly of claim 13, wherein the sensor generates a signal and the controlling means includes means for comparing the signal from the sensor to a reference signal indicative of a selected area of interest, the controlling means generating the first control signal when the signal from the sensor and the reference signal are not substantially equivalent and the controlling means generating the second control signal when the signal and the reference signal are substantially equivalent.

18. The assembly of claim 13, further comprising treating means coupled to the directable member in close proximity to the distal end of the directable member for treating the area of interest.

19. The assembly of claim 18, further comprising a treatment source coupled to the treating means for delivering a treatment to the area of interest through the treating means when the tip portion of the directable member is directed toward the area of interest.

20. The assembly of claim 13, further comprising an indicator for providing an indication that the area of interest has been detected by the sensing means, and means for coupling the indicator to the sensing means.

* * * * *